United States Patent [19]

Howson et al.

[11] Patent Number: 5,088,981
[45] Date of Patent: Feb. 18, 1992

[54] SAFETY ENHANCED DEVICE AND METHOD FOR EFFECTING APPLICATION OF A THERAPEUTIC AGENT

[76] Inventors: David C. Howson, 253 S. Adams St., Denver, Colo. 80206; Andrew D. Smith, 1570 Quince Ave.; Richard A. Simonelli, 279 Green Meadow La.; both of Boulder, Colo. 80302

[21] Appl. No.: 80,405

[22] Filed: Jul. 31, 1987

Related U.S. Application Data

[63] Continuation-in-part of Ser. No. 68,032, Jun. 29, 1987, Pat. No. 4,810,243, which is a continuation of Ser. No. 692,895, Jan. 18, 1985, Pat. No. 4,676,776.

[51] Int. Cl.⁵ ............................................. A61M 1/00
[52] U.S. Cl. ....................................... 604/31; 604/67; 128/DIG. 13
[58] Field of Search .............................. 604/31, 48–53, 604/65–67, 80, 90, 93, 95, 119, 12, 154, 246; 128/DIG. 12, DIG. 13

[56] References Cited

U.S. PATENT DOCUMENTS

| | | | |
|---|---|---|---|
| 3,737,251 | 6/1973 | Berman | 417/12 |
| 3,809,871 | 5/1974 | Howard et al. | 235/151.3 |
| 4,094,318 | 6/1978 | Burke et al. | 604/65 |
| 4,245,634 | 1/1981 | Albisser et al. | 604/66 |
| 4,270,552 | 6/1981 | Franetzki | 128/213 |
| 4,280,494 | 7/1981 | Cosgrove, Jr. et al. | 604/66 |
| 4,308,866 | 1/1982 | Jelliffe et al. | 604/67 |
| 4,391,598 | 7/1983 | Thompson | 604/65 |
| 4,494,950 | 1/1985 | Fischell | 604/66 |
| 4,498,843 | 2/1985 | Schneider et al. | 604/65 |
| 4,504,263 | 3/1985 | Steuer et al. | 604/65 |
| 4,515,584 | 5/1985 | Abe et al. | 604/66 |
| 4,543,955 | 10/1985 | Schroeppel | 604/66 |
| 4,551,133 | 11/1985 | Zeger's de Beyl et al. | 604/66 |

FOREIGN PATENT DOCUMENTS

WO84894 3/1989 PCT Int'l Appl. .

OTHER PUBLICATIONS

"A Package of Time Shared Computer Programs for Patient Care" by R. Jelliffe et al, First Annual Symposium on Computer Applications in Medical Care 10/3/77–10/5/77 Washington, DC.

Primary Examiner—Max Hindenburg
Assistant Examiner—John P. Lacyk

[57] ABSTRACT

Safety enhanced device and method are disclosed for effecting application of a therapeutic agent. A removable and operationally non-volatile programmable element is used to control operation of a therapeutic agent delivery unit. A computer, operationally independent of the delivery unit, is utilized to establish coded information for programming of the programmable element while removed from the delivery unit. Operation of the delivery unit according to the program then established for the programmable element is simulated at the computer prior to actual programming of the programmable element to insure the integrity of subsequent delivery of the therapeutic agent to a patient by the delivery unit. The programmable element effects independent delivery of therapeutic agents in each of a plurality of channels under the control of the programmable element. The programmable element is programmed to establish a flow profile that is customized for a particular patient during each minute of each day, and patient demand for therapeutic agents can also be accommodated with safeguards being included to assure proper dispensing.

25 Claims, 9 Drawing Sheets

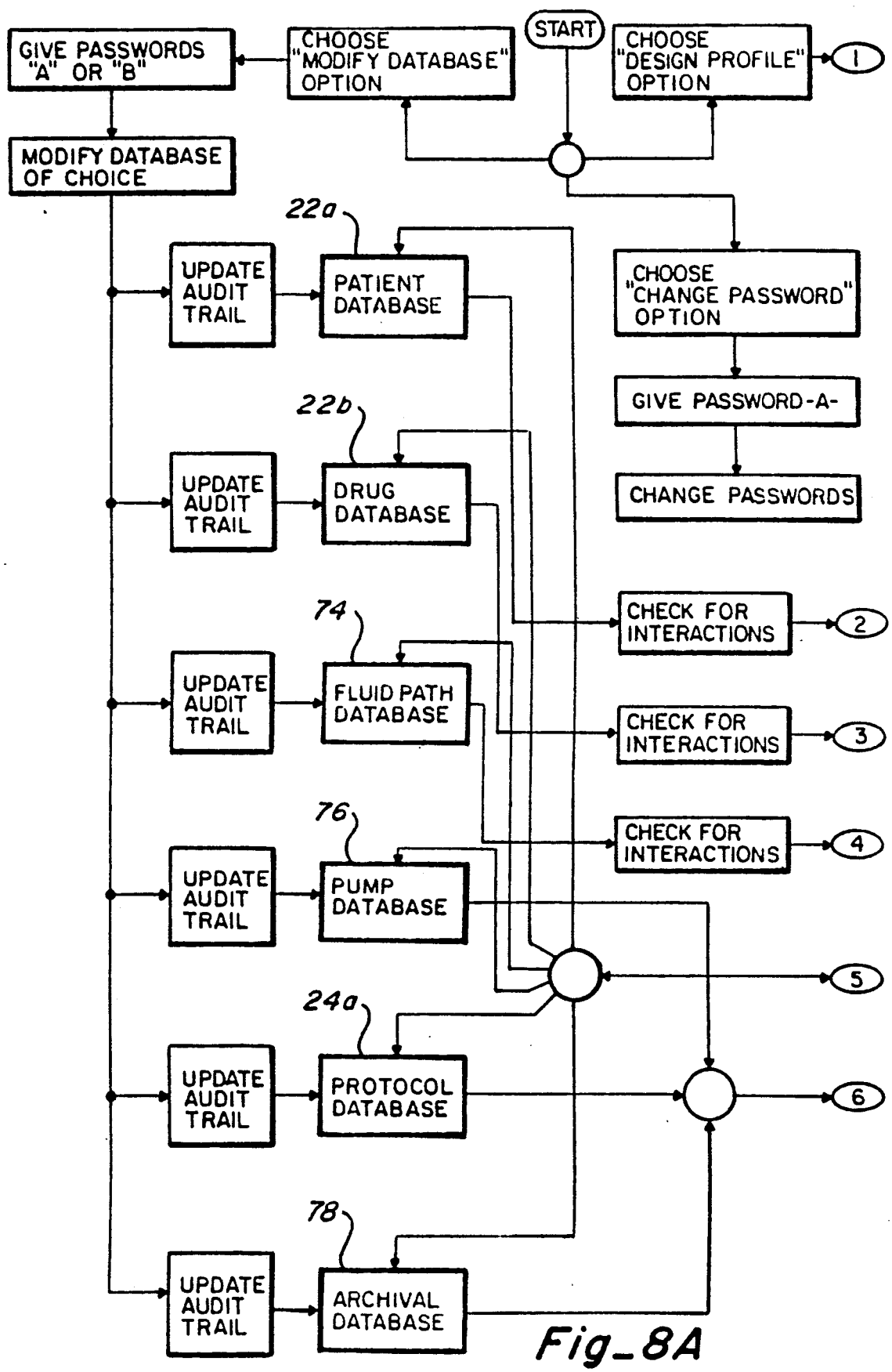
Fig_8A

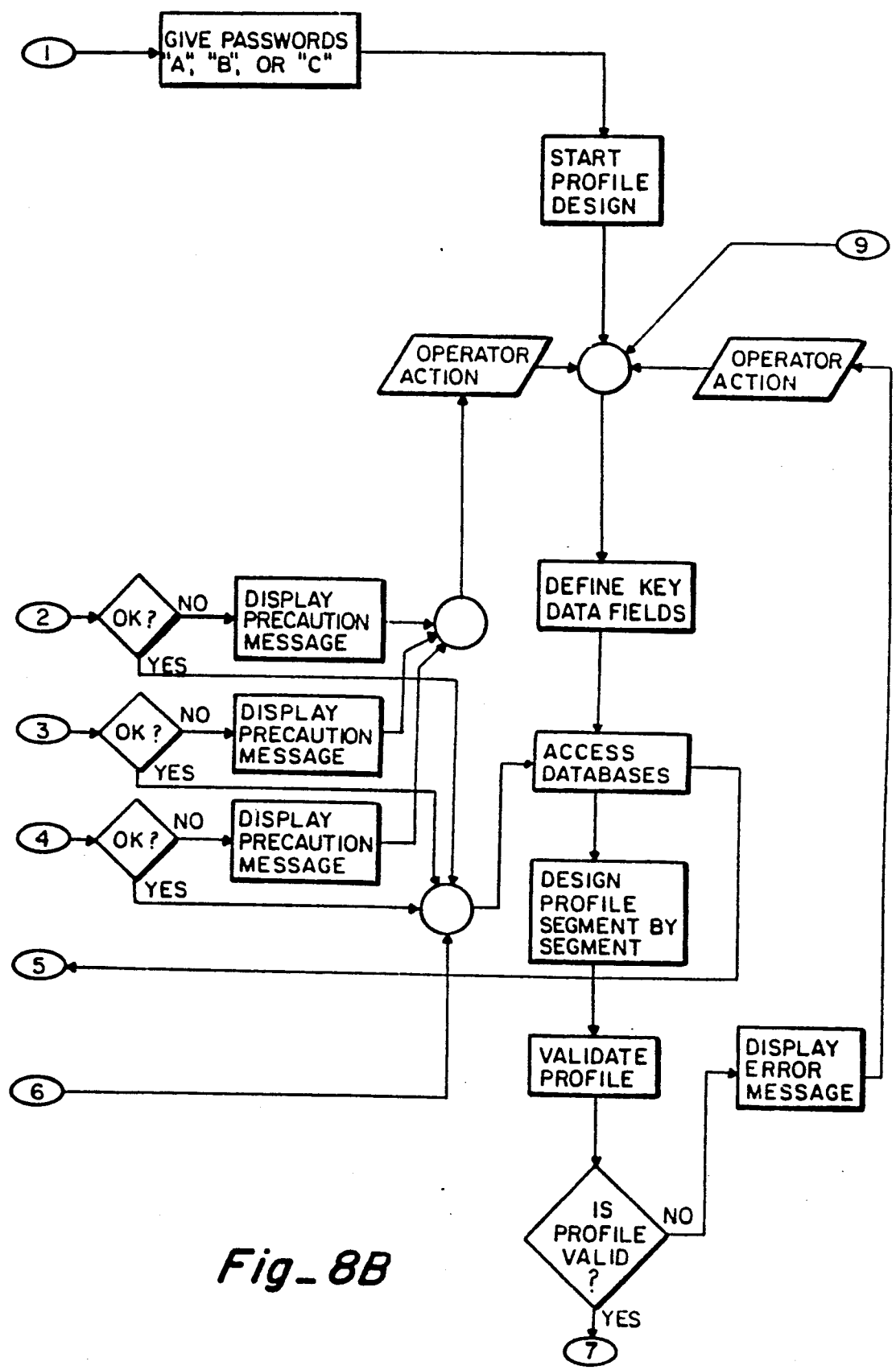
Fig_8B

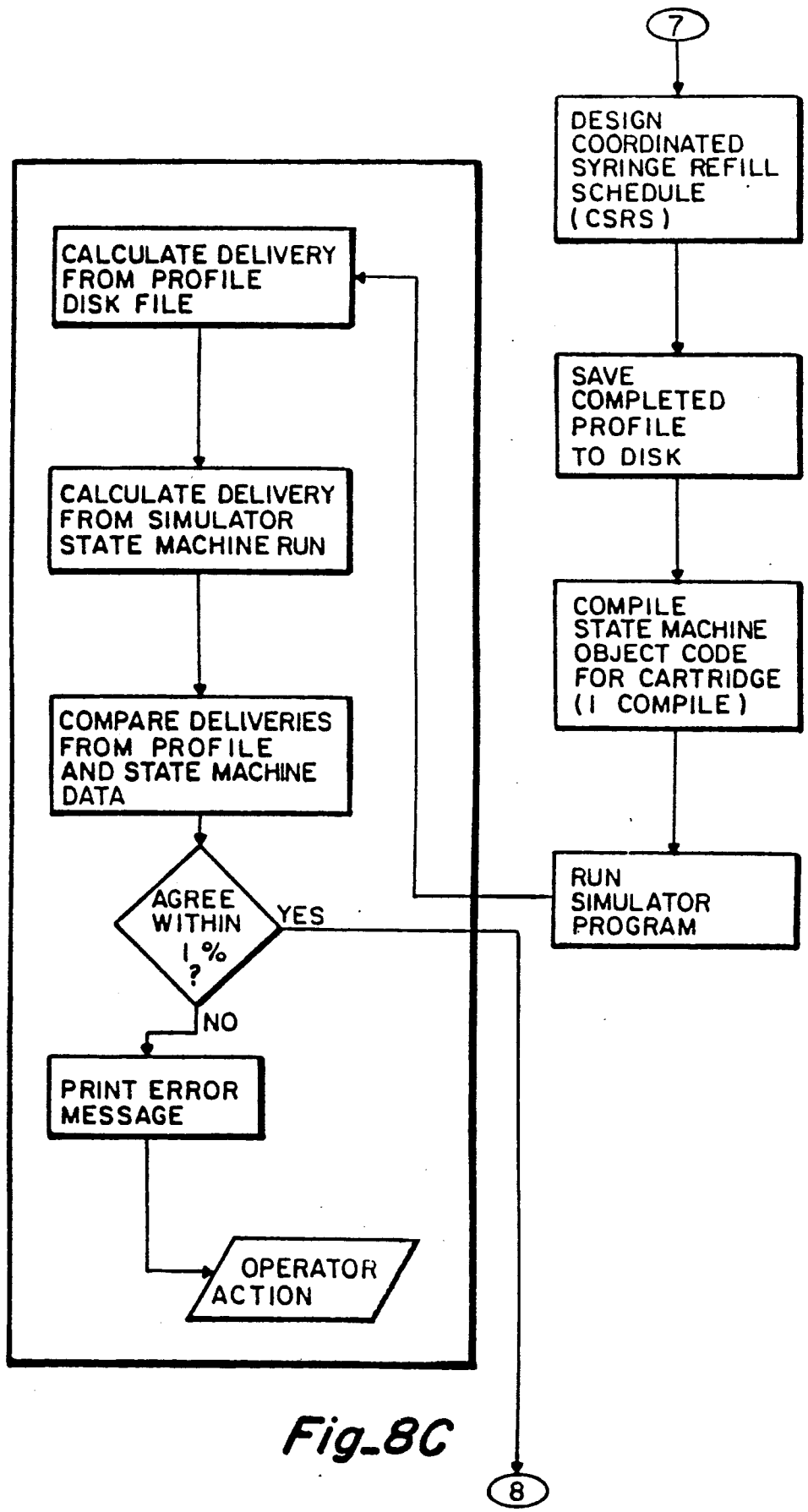
Fig_8C

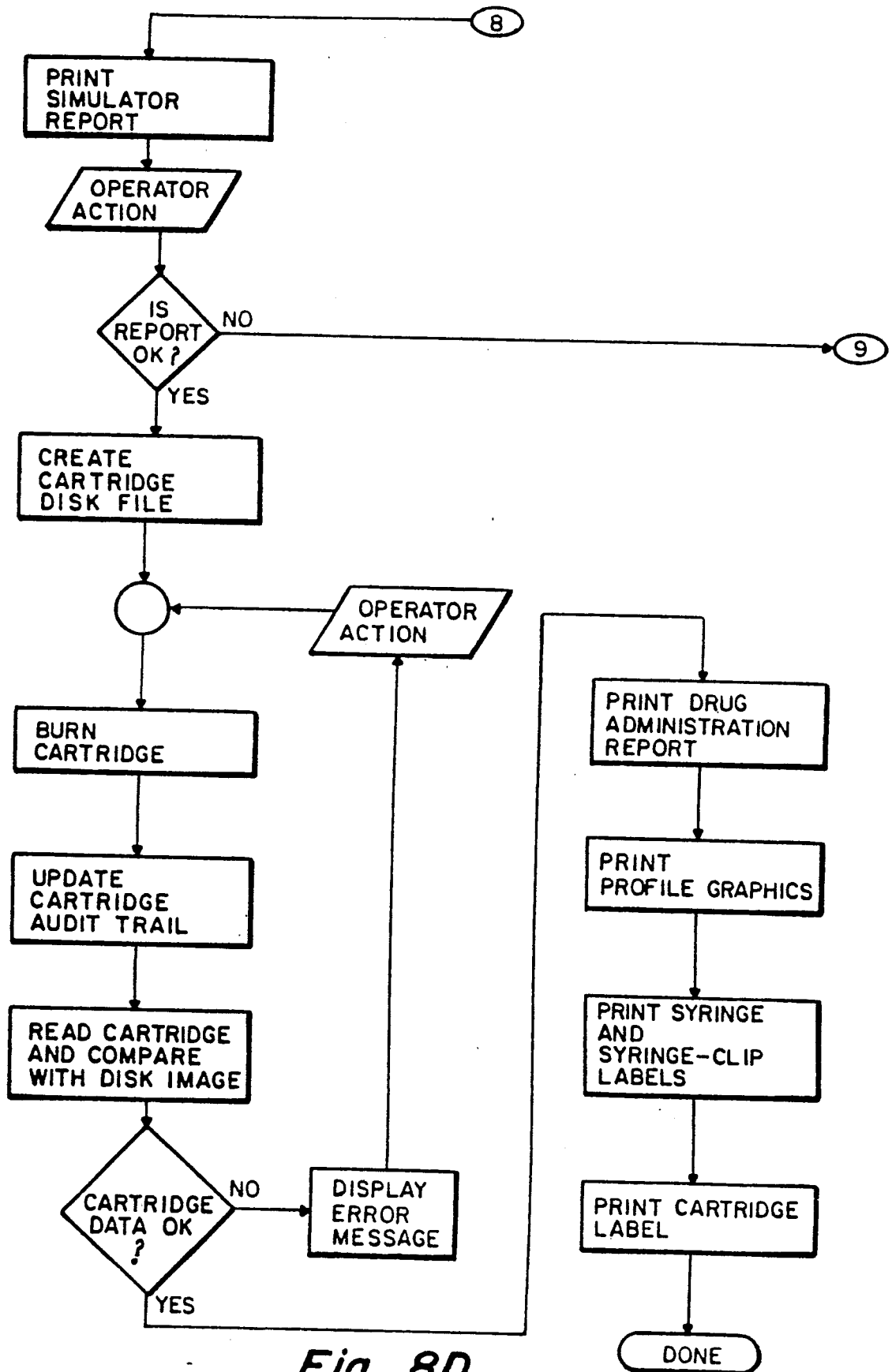
Fig_8D

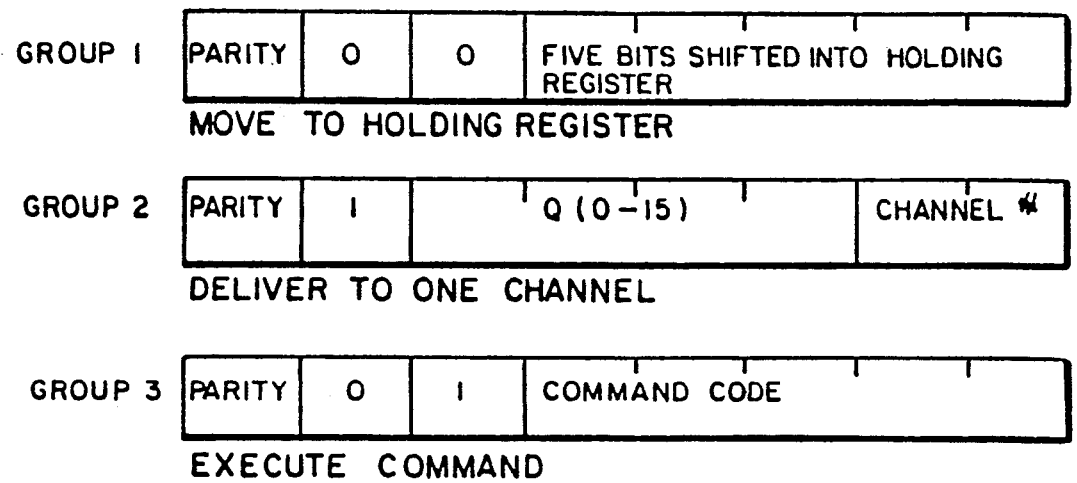
Fig_9
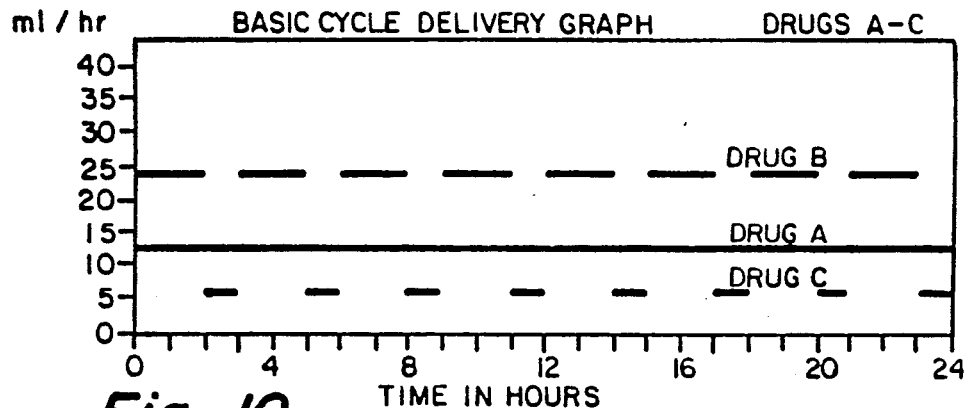
Fig_10
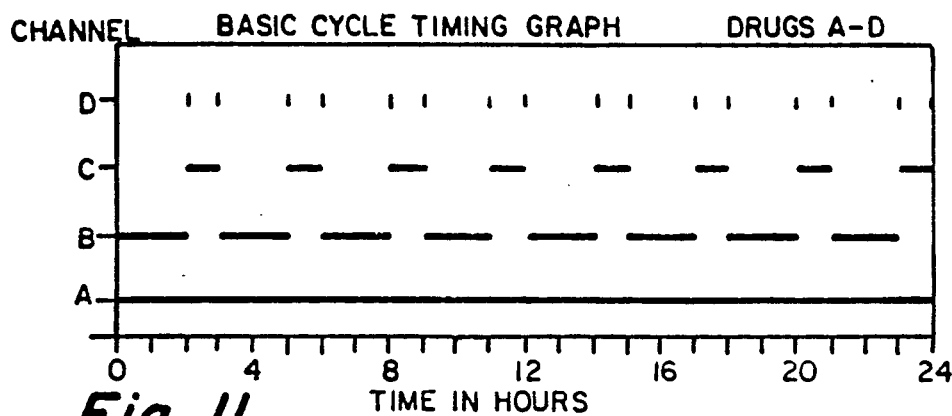
Fig_11

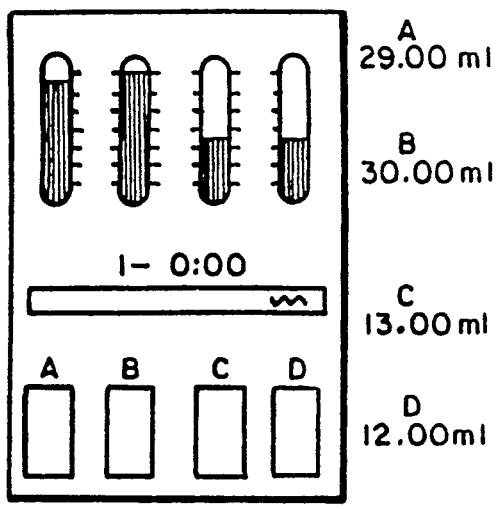
Fig_12A
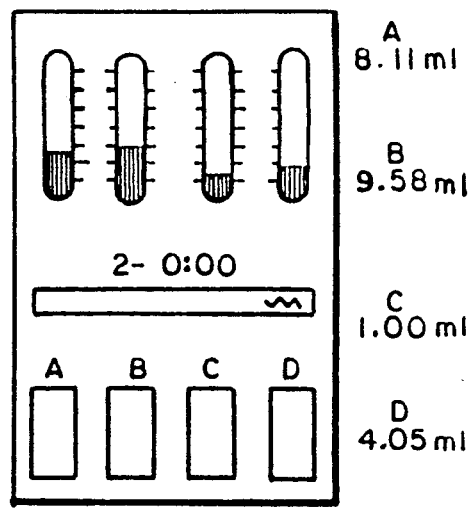
Fig_12B
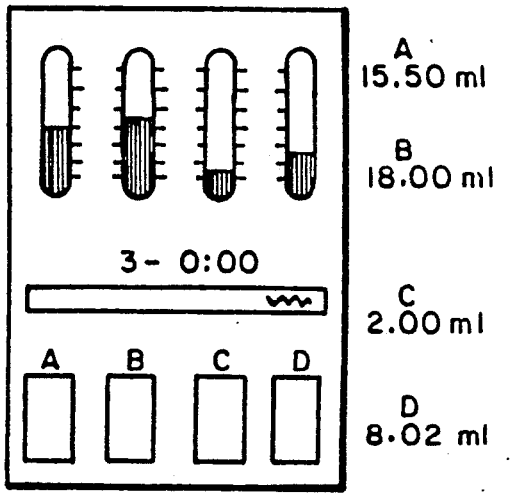
Fig_12C
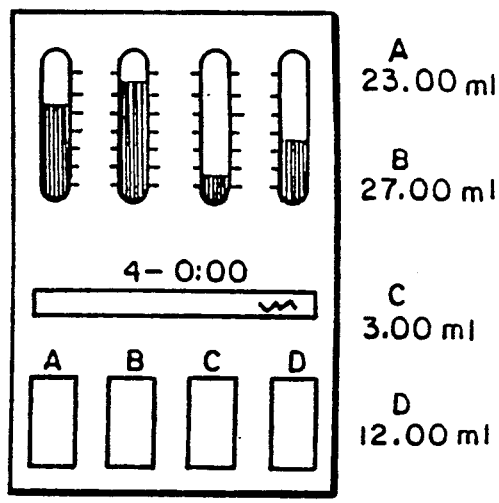
Fig_12D
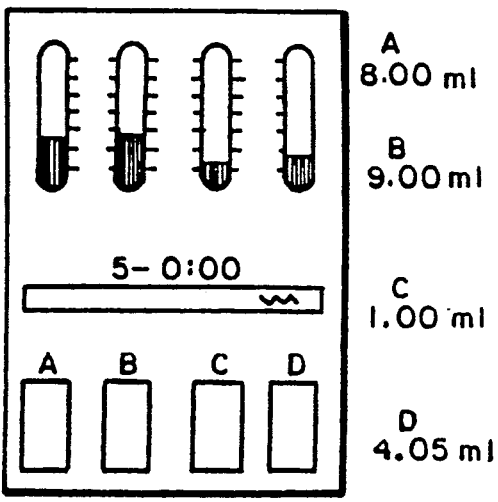
Fig_12E

SAFETY ENHANCED DEVICE AND METHOD FOR EFFECTING APPLICATION OF A THERAPEUTIC AGENT

RELATED APPLICATIONS

This application is a continuation-in-part of U.S. patent application Ser. No. 068,032, filed June 29, 1987, and entitled DEVICE AND METHOD FOR EFFECTING APPLICATION OF A THERAPEUTIC AGENT which is now U.S. Pat. Ser. No. 4,810,243, which application is a continuation of U.S. patent application Ser. No. 692,895, filed Jan. 18, 1985 and issued as U.S. Pat. No. 4,676,776 on June 30, 1987.

FIELD OF THE INVENTION

This invention relates to device and method for effecting application of therapeutic agents to a patient, and, more particularly, related to a safety enhanced device a method for effecting application of therepeutic agents to a patient.

BACKGROUND OF THE INVENTION

Various devices and methods have been heretofore suggested and/or utilized to control delivery of therapeutic agents, such as drugs, to a patient. In addition, various drive mechanisms have heretofore been suggested and/or utilized to effect metering of therapeutic agents to a patient, and various on-board dedicated controllers have also been heretofore suggested and/or utilized.

While improvements in dedicated, self-contained controllers have heretofore been made and/or suggested, meaningful further improvements have presented a problem, primarily due to space limitations which have become more acute as the desire and/or need for smaller sized devices has increased while, at the same time, the desirability and/or need for elements providing increasingly sophisticated complexity, which often require additional space, has also increased to the extent that such elements cannot be fitted into this decreasingly available space.

This has resulted in compromises that often have proved to be undesirable, at least in some respects. For example, at least some delivery units capable of delivering therapeutic agents in liquid form and small enough to be worn on the body of a patient must normally now be single-channeled devices, and at least some such devices have normally been limited to delivery of a therapeutic agent at either a controlled rate or a cycled bolus, with the rate being manually adjustable or automatically changed to programmed levels only up to a few times in any twenty-four hour period (with provision being also sometimes made for a brief supplemental bolus of varying size upon demand by the patient or amplitude release on demand of the patient when combined with a profile of a programmed waveform).

Known systems and methods for programming and controlling delivery units have varied, but generally include a manual knob or pushbutton, or buttons on a keyboard, which adjust parameterrs, and the values of which may be displayed on a panel.

Ambulatory delivery devices capable of delivering therapeutic agents in liquid form have also been heretofore suggested and/or utilized. Within this category are delivery units that are implanted into the body of a patient. Such devices have been typically passive type devices (such as pressurized medication delivery devices) or have been adapted from cardiac pacemaker technology, and flow profile programs for these units have normally been communicated telemetrically to the unit by a programmer. Several such existing devices use the approach of a keyboard remote to the delivery unit, while others use a large, desktop special-purpose computer connected with a telemetry antenna, with such telemetry using pulse-modulated electromagnetic fields.

The programs contained within such dedicated computers are designed with a limited number of preprogrammed waveforms. Because of the use of a limited selection of predetermined profiles, these computers are, in effect, an extension of manual keyboards, and do not give the user either the capability of specifying the profile waveform itself, or of combining freely-defined waveform components. Moreover, these programmers are usually further limited to programming single-chamber devices.

The telemetered programming system described above use "random access memory" (RAM) units to store the transmitted data in the delivery unit. RAM units, however, have inherent disadvantages, which include the need for sustained power to avoid loss of memory contents, and are designed for ease and speed of writing into memory as well as reading the memory contents which results in relatively high susceptibility to transient electromagnetic noise.

Such programmable devices most often require the use of microprocessors (which depend upon a separate machine program to operate) as well as a program of user-defined parameters. Changing flow profiles in most of these devices entails rewriting the machine program as well as the user program. The machine program is, however, not accessible to reprogramming by the user, and the program must therefore be physically replaced since it is normally contained in a "read only memory" (ROM) unit that is incapable of being reprogrammed (or is reprogrammable only after physical removal and special procedures).

In addition, the relative complexity of the machine programs needed for such general-purpose microprocessors does not easily allow unambiguous proof of all possible logical states of the processor. While such proof is possible in theory, it is extremely difficult to demonstrate in reality, and very expensive to implement. Such proof is therefore limited to relatively simple logic networks and programs, that are far below the complexity of the typically-used microprocessor and machine program.

More recently, dual microprocessors have been used to compensate for the failure potential inherent in single-processor designs, in order to assure only safe failure modes. This does not, however, resolve the problem of ambiguity, and creates a trap for logic states not explicitly contained in a truth table used for comparison.

Since known devices are specially designed programming computers, they tend to be very limited in their capability and the difficulty of writing programs for such computers is very high. In addition, known devices provide only the minimum functions needed to program the delivery unit, and do not provide assistive programs or databases.

The status of known devices intended for table or pole mounting, and used with relatively high flow rates, is somewhat different than for ambulatory devices. Such known large-volume delivery units, however, normally provide only constant flow rate profiles or combinations thereof. Also, the controls for such devices are normally local on-board, and are typically of the keyboard variety which are used in conjunction with various data displays. Also typically, currently used devices have microprocessor controls, with the most advanced systems using dual processors for error detection.

In such devices, a plurality of flow channels have been provided. Typically, however, a primary channel is used to supply a fluid which is usually delivered in large volumes, and a secondary channel is used to supply a smaller volume of a drug containing fluid (see, for example, U.S. Pat. No. 4,391,598 to Thompson). In this system, the fluid flow in the primary channel is interrupted only when a manual order is given which also causes commencement of flow through the secondary channel, and after flow through the secondary channel has occurred at a known flow rate for a time period calculated to be coincident with the emptying of the reservoir associated with the secondary channel, flow is reverted back to the primary channel. In addition, the flow rate in each channel is constant and set by the user with on-board controls.

Another form of multi-channel device has also been suggested in which the flow rate in each channel is a fixed ratio to that of the other channels, depending upon selection of mechanical elements (see, for example, U.S. Pat. No. 3,737,251 to Berman et al).

Another large delivery unit has been suggested which can control up to four flow channels, but utilizes a constant flow rate for each channel that is set using on-board controls.

A single-channel delivery unit has been suggested which has connectors provided for computer access. However, the delivery unit and computer are not designed together as a system. Instead, a user must first provide a computer, and then program the computer for the intended purpose, with communication between the delivery unit and computer being effected by direct wire or telemetry connection.

A device having a delivery unit with a central processing unit that includes a volatile random access memory (RAM) unit and a program-carrying read only memory (ROM) unit, and with the device being programmable by a user or by an electronic data processor connected therewith, is shown in U.S. Pat. No. 4,308,866 (Jelliffee et al).

In addition, programmable physiological infusion is disclosed in U.S. Pat. No. 3,809,871 wherein a paper tape (or paper punch tape or magnetic tape) is prepared untilizing a computer program and the thus prepared tape is then utilized to control operation of an infusion pump. Also, it has heretofore been suggested that a cam can be contoured as needed and then utilized to control delivery during intravenous feeding (see U.S. Pat. No. 4,091,810 to Lundquist).

A need still exists, however, to provide a device and method for effecting delivery of a therapeutic agent, particularly in a complex manner and a long time duration, wherein the delivery unit can be controlled by a remotely programmable non-volatile element in a manner to enhance safe operation of the delivery unit.

SUMMARY OF THE INVENTION

This invention provides a safety enhanced system and method for application of one or more therapeutic agents to a patent which overcomes many of the disadvantages of known devices and methods such as set forth hereinabove.

A computer, such as a general purpose computer, is used to establish coded information for programming of a programmable element, and operation of the delivery unit, according to the then established program for the programmable unit, is simulated and the calculated simulation results compared with the calculated delivery according to the then desired profile are compared at the computer prior to actual programming of the programmable element, which element is programmed remotely from the delivery unit (which can be a pump). The programmable element, after placement in the delivery unit, controls operation of the delivery unit, which delivery unit may contain a plurality of channels all of which are controlled by the programmable element to effect delivery of a plurality of therapeutic agents.

Through use of this arrangement, the device and method of this invention allows programming of a therapeutic agent delivery unit (single or multi-channel) to safely deliver virtually any needed or desired fluid flow rate profile, normally as a function of time, with such profiles being definable by the user or selected from a database of profiles that does not require machine modification of the delivery unit. Patient or event triggering capability is also provided, with safeguards, to allow introduction of supplemental profiles, which are later automatically terminated and flow returned to control by the programmed profile, and each channel is independently or contingently controllable under fully automatic and unattended operation.

In addition, manual control functions or special profiles assigned by programming may also be provided, and secure, verifiable means of transmission of data from the data entry means to the delivery unit are utilized, which transmission means requires neither electrical power to sustain its contents nor continued connection between data entry means and delivery means.

Since the data entry means is based on a general-purpose computer, the difficultly the writing applications software is minimized, and assistive programs are also provided in the data entry means to aid the user in specifying the desired flow profile (including, if desired, graphics-based entry means), with provision being made to simulate the action of the delivery unit, both physically and pharmacokinetically. Extensive error-reducting means including use of databases for cross-checking drug information, protocol parameters, and patient records is also provided, and dosage adjustment assistance may be provided based on labroatory blood values by use of pharmacokinetic algorithms (or through the use of special calculators enabling the patient to apply results of test done in the home or other non-laboratory environment) for fine adjustments of the dosage scale.

The system and method of this invention thus permits virtually unlimited programming capabilities without compromising the size and weight of the delivery unit while enhancing safe delivery of the therapeutic agent or agents from the delivery unit. Thus, by freeing the system from size constraint, virtually unlimited programming capabilities may be included within the system, and yet the delivery unit (which may be worn by the patient) can be smaller than even less sophisticated devices and yet safely delivery therapeutic agents.

This unlimited programming capability, or power, thus provides an ability to program single or multiple channels with each of the multiple channels being capable of having different drugs and individually specified delivery profiles and with the machine code of the delivery unit being automatically and safely programmed for each channel, as well as an ability to safely assign, by programming, manual or event synchronized input sources to any designated delivery channel.

It is therefore an object of this invention to provide an improved and safety enhanced system and method for application of a therapeutic agent to a patient.

It is another object of this invention to provide an improved and safety enhanced system and method for application of a therapeutic agent to a patient wherein a programmable logic unit is programmed remote from the delivery unit and then used at the delivery unit for controlling operation of the delivery unit.

It is another object of this invention to provide an improved system and method for application of a therapeutic agent to a patient that allows safe delivery of any selected flow rate profile with programming of a programmable logic unit being carried out remotely of the delivery unit and the delivery unit being virtually free of size restraints other than being adapted to receive the programmable logic unit.

It is still another object of this invention to provide an improved and safety enhanced system and method for application of a therapeutic agent to a patient wherein a programmable logic unit is used to individually control operation of a plurality of channels in the delivery unit.

It is yet another object of this invention to provide an improved and safety enhanced system and method for application of a therapeutic agent to a patient wherein a computer establishes a desired program and the operation of the delivery unit is simulated and compared with the then established and desired program prior to programming a programmable element that is later used to control operation of the delivery unit.

With these and other objects in view, which will become apparent to one skilled in the art as the description proceeds, this invention resides in the novel construction, combination, arrangement of parts and method substantially as hereinafter described and more particularly defined by the appended claims, it being understood that changes are meant to be included as come within the scope of the claims.

DESCRIPTION OF THE DRAWINGS

The accompanying drawings illustrate a complete embodiment of the invention according to the best mode so far devised for the practical application of the principles thereof and in which:

FIGS. 8A through 8D, taken together, form a functional flow diagram enabling the computer to program a programmable element in a safety enhanced manner;

FIG. 9 illustrates state machine codes for the programmable element by groups wherein the programmable element is a PROM cartridge and the delivery unit is a syringe device having an instruction set of thirty-two instructions;

FIG. 10 are typical basic cycle delivery graphs for a delivery unit under assumed conditions;

FIG. 11 is a typical basic cycle timing graph for a delivery unit under assumed conditions; and FIGS. 12A through 12E are typical flow delivery indications viewable at the delivery unit for specific times over a typical five day delivery period.

DESCRIPTION OF THE INVENTION

Figure 1:
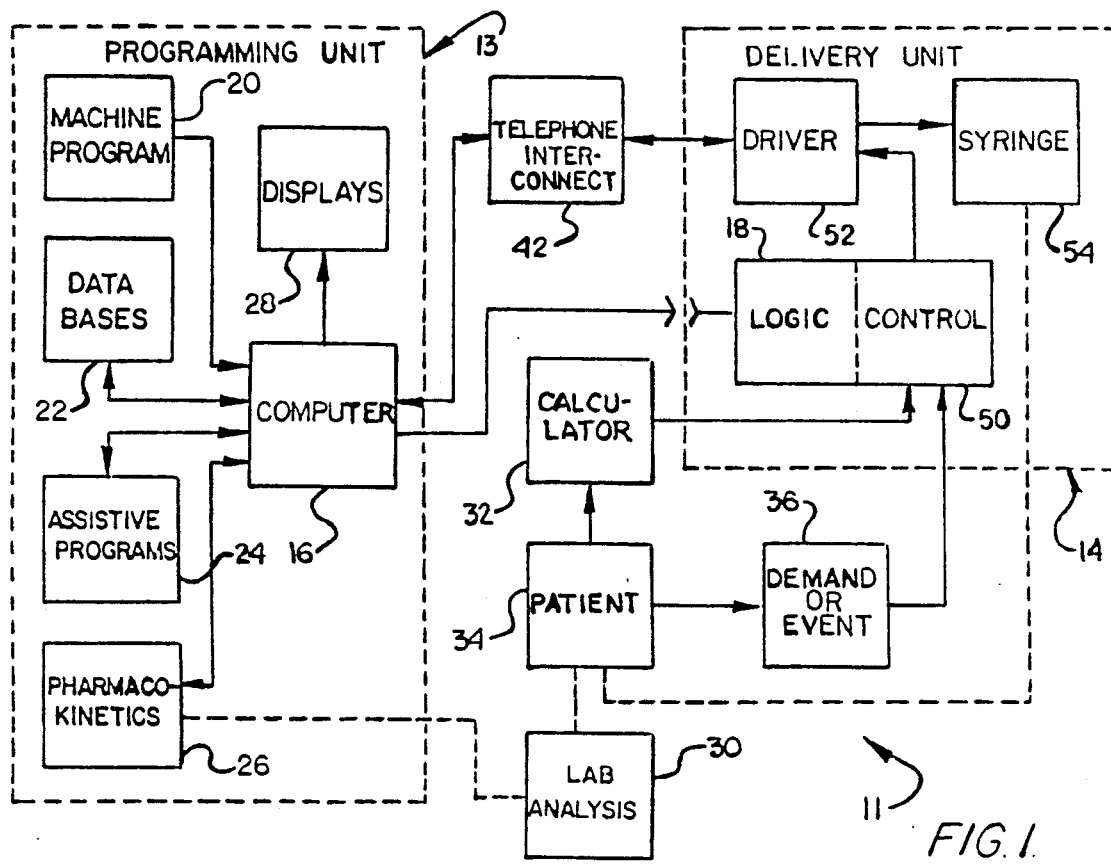
FIG. 1 is a overall block diagram of the device of this invention with patient interaction being also indicated.

The block diagram of FIG. 1 summarizes the interconnection the components, or elements, of a device utilizable according to of this invention. As shown, device 11 includes a programming unit 13 and a delivery unit 14.

Programming unit 13 includes a computer 16, preferably a general-purpose computer, that is capable of programming programmable logic unit 18 used to control operation of delivery unit 14 when placed in delivery unit 14 (as indicated in FIG. 1). As also indicated in FIG. 1, by way of example, computer 16 preferably has machine program 20 connected therewith, as well as various databases 22, assistive programs 24 and pharmacokinetic programs 26, as needed, for programming the logic unit, as is brought out more fully hereinafter.

Obviously, computer 16 could also have connected therewith any number of other input devices, such as a keyboard, graphics, tablet, joystick, "mouse", or other manipulanda, or other data acquisition devices. In addition, computer 16 can also be connected with one or more displays 28, which, by way of example, could be a video screen, a liquid crystal display, a printer and/or or a plotter.

Logic unit 18 is preferably a programmable logic cartridge. Programmable logic cartridge 18 may be any form of non-volatile logic (meaning the programmed form will be retained in the absence of electrical power) or otherwise volatile logic sustained by an accompanying power source, such as a small back-up battery. Preferred forms or such components include, but are not meant to be limited to, commercially available devices such as programmable read only memories (PROMs), erasable programmable read only memories (EPROMs), electrically erasable programmable read only memories (EEPROMs), electrically alterable programmable read only memories (EAPROMs), non-volatile random access memories (NVRAMs), and programmable logic arrays (PLAs).

The logic cartridge contains the configurable portion of the logic path of the control unit and establishes operation thereof depending upon the contained configuration of logic gates or states in the delivery unit. Program 20 is a machine program that is used to operate computer 16, and the system transforms the user-provided information into a logic configuration suitable for operating the delivery unit in accordance with the intended delivery requirements of the user. Computer 16 then writes the configuration into logic cartridge 18 and automatically verifies correct entry, as is also brought out more fully hereinafter.

Figure 2:
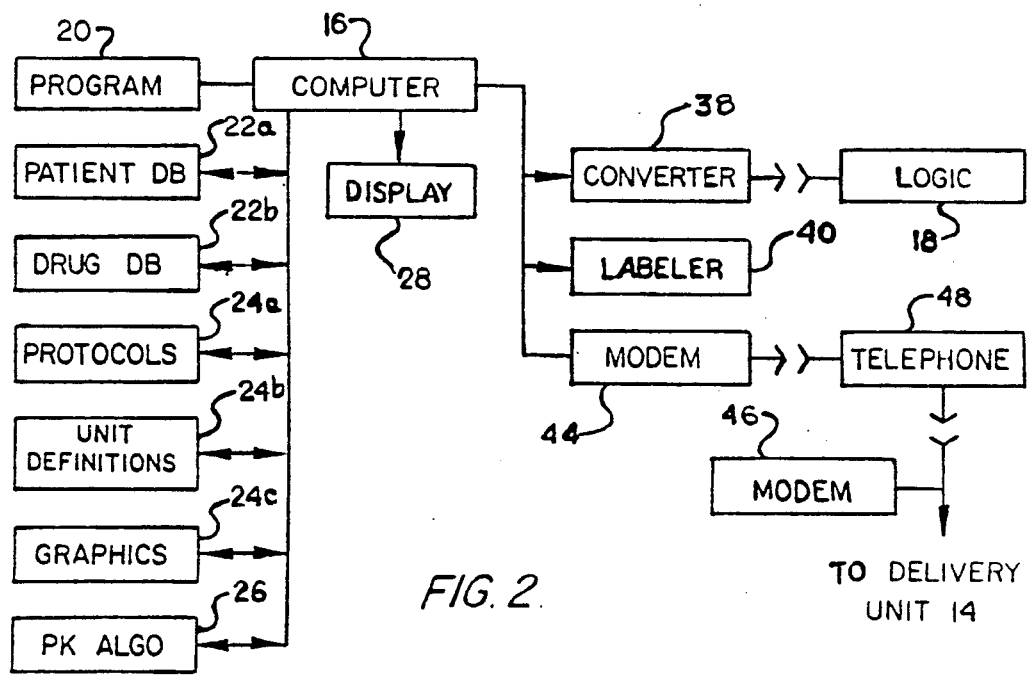
FIG. 2 is an expanded block diagram of the programming unit shown in FIG. 1.

In assisting the user to enter error-free information, the computer uses appropriate databases 22 and assistive programs 24 to determine inconsistencies, to offer the user supporting information and/or to aid calculations, as indicated in greater detail in FIG. 2. Databases 22 can therefore include, by way of example, patient DBs 22a and drug DBs 22b. These can be augmented by assistive programs 24 (such as protocols 24a, unit definitions 24b, and graphics 24c), and by pharmacokinetic algorithms 26 to thereby provide information such as accepted drug dosage ranges, interactions between drugs when present in the patient at the same time, and parameters for mathematical dose-response or pharmacokinetic models for each drug.

By using these databases and assistive programs, the computer is able to automatically interpolate from the preferred nomenclature of the user and units of measurement to those needed by the logic of the delivery unit (heretofore, the user was required to perform numerous calculations before being able to adjust a delivery unit, each such calculation carrying a finite probability of introducing error).

The computer is also able to utilize the databases to retain the history of the individual patient's treatment and responses, and the patient's pertinent physiological or other parameters used to assist determination of safe and effective dosage. Furthermore, the computer uses a "library" of delivery protocols, either provided by the manufacturer, developed by the user, or provided by a third party. Such protocols assist the user by requiring only the minimum amount of data needed to correctly adjust the dosage to an individual patient.

The computer may also use pharmacokinetic, pharmacodynamic, or dose-response models (designated generally by the numeral 26 in FIGS. 1 and 2), to either aid programming of the delivery profile of the delivery unit, or to simulate the outcome of a profile in terms of resulting bodily concentrations of the delivered substances, or both. Furthermore, such programs may aid the user in finally adjusting dosages after taking requirements of substance concentrations within the body of the patient at some time intervals after beginning delivery. Such data may be acquired from a clinical setting, such as a hospital laboratory 30, as generally indicated in FIG. 1, or in the patient's own normal surroundings by means of simplified tests.

Data may then be entered into the programming computer for programming a new logic cartridge, or may be communicated to the delivery unit. In the latter case, the logic cartridge contains sections of configurable logic suitably different from the base configurations so as to allow small changes in effective dosage rates from the base program.

The suitable interpolation of a concentration measurement to a logic configuration or selection is normally automatically accomplished in the programming computer, but may be accomplished by a calculator 32 (operated by patient 34) which has the ability to communicate with the delivery unit under special circumstances such as, for example, in response to patient perception of clinical symptoms.

As brought out more fully hereinafter, a patient, or an event, is also able to initiate delivery of the therapeutic agent, as generally indicated in FIG. 1 by the block entitled demand or event 36, the output from which is coupled to delivery unit 14.

As also indicated in FIG. 2, data is written into logic cartridge 18 by computer 16 through converter 38, with the computer also providing, if desired, an output to labeler 40 (which provides a suitable label for attachment to the logic cartridge). As also indicated in FIG. 2, computer 16 may also be connected with delivery unit 14 through a telephone interconnect system 42 that includes modems 44 and 46 at opposite sides of telephone system 48, for purposes as described more fully hereinafter.

Delivery unit 14 includes a control unit 50 which receives removable programmable logic unit 18. Control unit 50 drives a driver 52, which driver, in turn, controls operation of an applicator, such as a syringe 54, through which the therapeutic agent is delivered to patient 34. Delivery unit 14 will not operate if logic unit 18 is removed from control unit 50.

The driver mechanism may be of any suitable form, and may be, for example, a mechanism that depresses the plunger of a syringe, as is now preferred, with all components contacted by the fluid drug formulation being preferably disposable.

Figure 3:
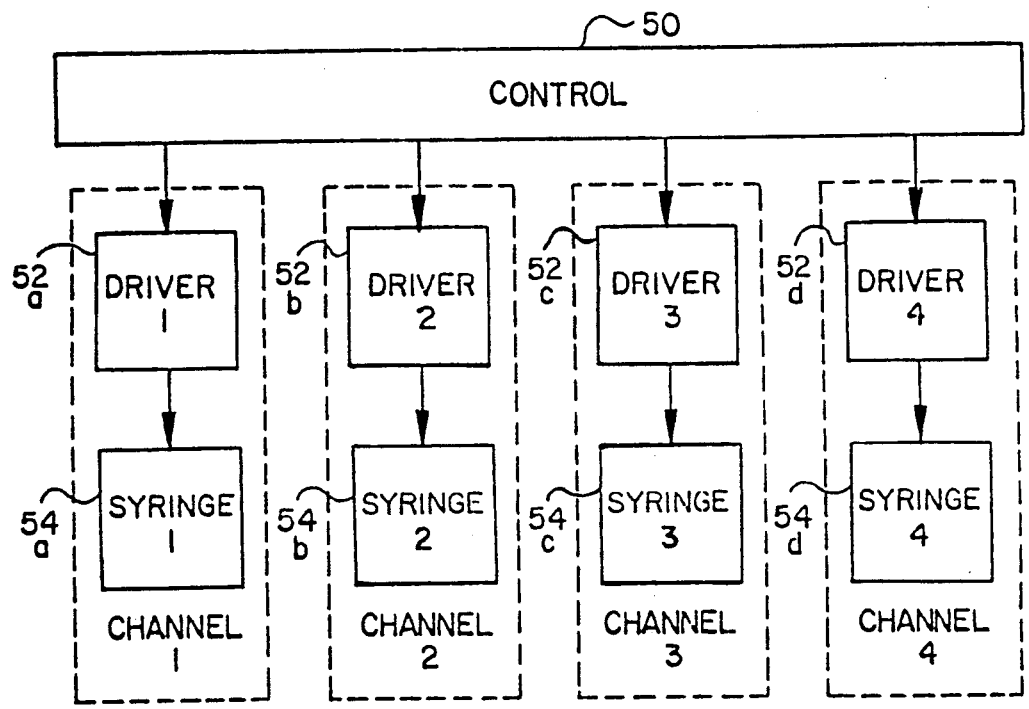
FIG. 3 is a block diagram of the delivery unit, similar to that shown in FIG. 1, but illustrating use of the control unit to control a plurality of channels through which therapeutic agents may be delivered to a patient.

The delivery unit may contain a plurality of independently controlled fluid delivery channels as indicated in FIG. 3. When so utilized, control unit 50 independently controls each driver (indicated by the numerals 52a–d in FIG. 3), and each driver controls a separate syringe (indicated by the numerals 54a–d in FIG. 3) with each driver and syringe establishing separate channels (indicated in FIG. 3 as channels 1-4).

The preferred embodiment uses a modular design assembly in which any number from one to four channels may be used at any one time. More than one delivery unit assembly may, however, be synchronized together for applications requiring more than four fluid channels.

In its preferred form, the controller logic consists of discrete logic elements so as to make up a state machine. This state machine performs strict sequences of logic functions depending upon the state of a clock or other control element, or a combination thereof, and upon the state of the logic programmed into the logic cartridge. Alternately, combinational logic can be utilized in a dedicated control machine, which again uses the configurable logic in the programmable cartridge to define the sequence of logic operations.

While the intended preferred embodiment of this invention utilizes a delivery unit without a microprocessor, the delivery unit could include a suitably programmed microprocessor (or microprocessors), which reads operating parameters from the information contained in the programmable memory cartridge which is programmed remote from the delivery unit, but such use would also introduce significant limitations.

The electronic controller 56 of control unit 50 also utilizes a read/write memory 58 (see FIG. 4) within the delivery unit to record data about the actual operating history over a time period, for example, a number of days, and can include coding of date and time of day, if desired. Such data are useful for various purposes, including diagnosing hardware problems, recording data of patient-demanded delivery events, recording data on physiologically or blood-level-controlled delivery profiles, and/or compiling data on the patient's compliance with a prescribed delivery schedule.

Figure 4:
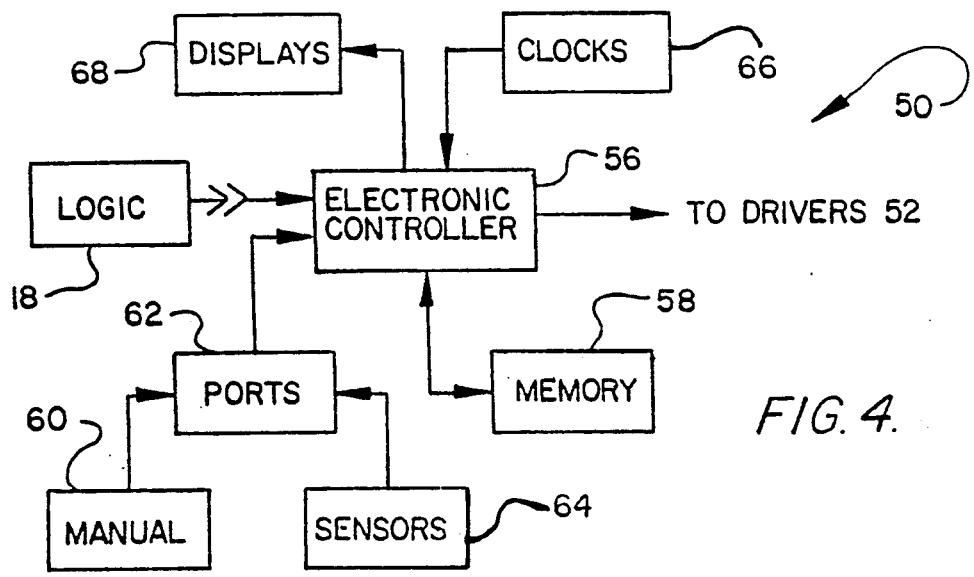
FIG. 4 is an expanded block diagram of the control unit shown in FIG. 1.

The delivery unit may, depending upon the application, use manually-operated controls 60 (connected through ports 62 to controller 56 as indicated in FIG. 4) to synchronize delivery events of any complexity with the detailed waveform and amplitude information relating to the events being programmed into the logic cartridge. Such manual controls may operate any of the available channels, the assignment being made by appropriately programming the logic cartridge.

Similarly, delivery events may be synchronized by detecting, as by sensors 64 as indicated in FIG. 4, the occurrence of a physiological event or by appearance of a critical level of a substance in the blood or other physiological fluid. Of greater complexity, the profile of fluid delivery over time may change in accordance with direct modulation from the detected levels and/or statistical behavior of physiological events, or from detected levels of substances in the blood or other physiological fluids.

The computer can also communicate with the delivery unit remotely by means of the telephone interconnect unit 42. In this case, communication is normally restricted to hardware problems diagnosis, routinely report patient usage information, or to slightly adjust dosage rate.

As also shown in FIG. 4, control unit 50 includes electronic controller 56 capable of dividing time into time segments, such as, for example, one-minute intervals, utilizing clocks 66. Typically, clocks 66 follows a twenty-four hour clock in real time. At each time segment, the controller addresses the logic cartridge and performs a series of housekeeping checks, then looks to see if a delivery event is scheduled. As also indicated in FIG. 4, the delivery unit can, if desired, include a display unit 68, but such display units are preferably not included, and instead the delivery unit includes display window 72, as indicated in FIGS. 12A through 12E to give a visual indication of the therapeutic agent then in each syringe 54.

Since the computer programs the logic cartridge, the computer preferably uses programs that translate the user's expression of delivery profile into time-encoded series of discrete segments.

Figure 5:
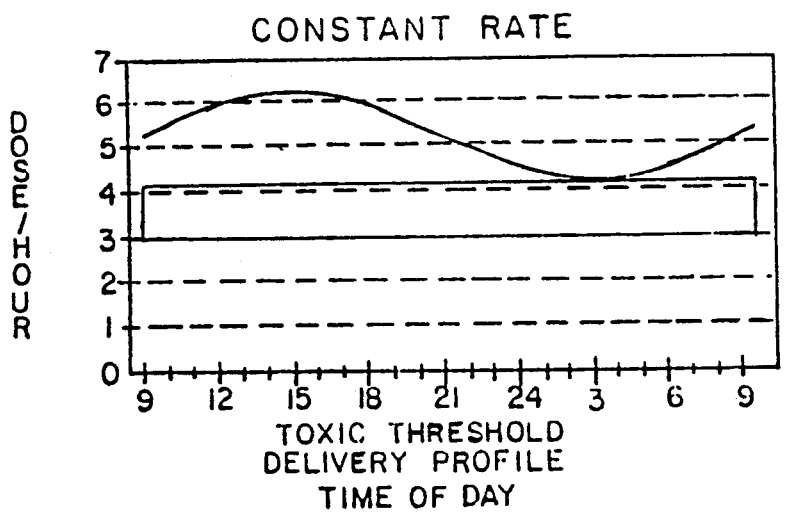
FIG. 5 is a graph illustrating a typical constant rate profile for therapeutic agent delivery during a one day period.
Figure 6:
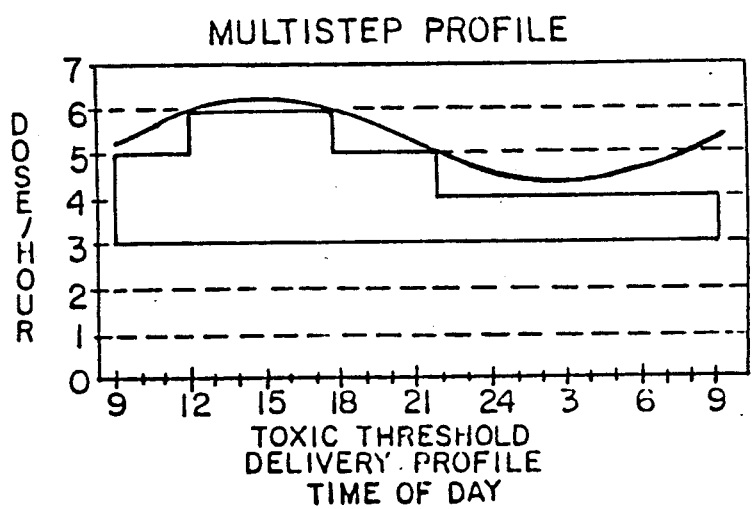
FIG. 6 is a graph illustrating a typical multilevel approximation to the toxicity limit for therapeutic agent delivery during a one day period.
Figure 7:
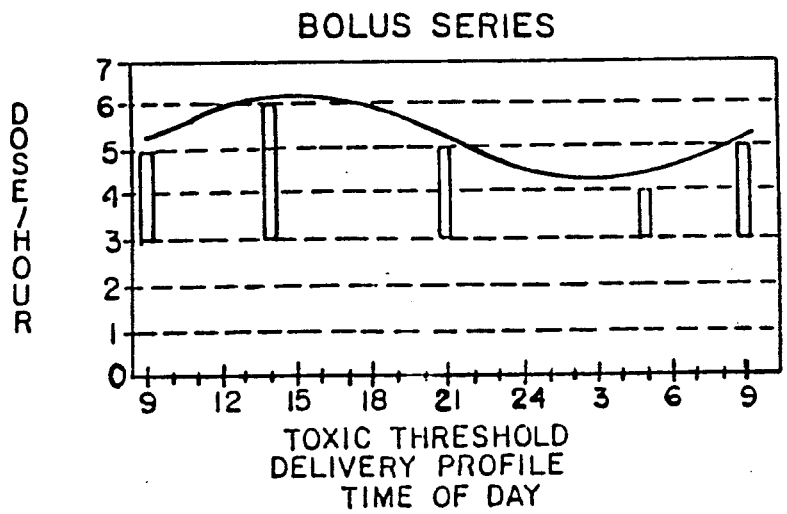
FIG. 7 is a graph illustrating a typical series of boli (discrete shots) of therapeutic agent delivery spaced over a one day period and illustrating limitations in dose rate due to varying toxic susceptibility.

Examples of some of the more simple profiles are shown in FIGS. 5, 6 and 7. In these examples, the wavelike top line represents an exemplary toxicity limit of a patient which limit varies with a twenty-four hour rhythm. The objective of optimizing flow rate is achieved by delivering the therapeutic agent at a rate which comes close to the toxic limit, but never exceeds it.

FIG. 5 shows a typical constant rate profile deliverable by many delivery systems now known, and FIG. 6 shows a typical multilevel approximation to toxicity limit, while FIG. 7 shows the results of a typical series of boli (discrete volumes) spaced variably in time and limited in dose content by the varying toxic susceptibility.

The delivery unit is not dependent upon the size or type of mechanical drive being used. The controller would work just as well with a small capacity element, such as, for example, a 0.1 cc/day capacity, as with a large capacity element, such as, for example, a 2000 cc/day capacity driver element. It would also work equally as well with other drive mechanisms, such as, for example, a pulsatile solenoid drive or a continuous-flow proportional regulator, as with the syringe drive.

Since the computer designs the delivery profile for each channel, based on the specifications of the user, not only can each channel be made to operate independently, the channels can also be linked in operation relative to one another to allow greater operating flexibility. For example, while a particular delivery unit might offer up to four channels of 30 cc of a therapeutic agent each, when two channels are operated in series or in tandem, the result is to allow 60 cc capacity for a particular therapeutic agent (such as a relatively insoluble drug, for example).

In a working embodiment of the device of this invention, a delivery unit, or pump, is utilized having four syringes the piston of each of which is driven by a different one of four different drive units to thereby effect delivery of therapeutic agents from the syringe in a precisely controlled manner. To effect such delivery, a logic cartridge (transfer element) is programmed according to this invention at the computer while the logic cartridge is removed from the delivery unit, and the thus programmed logic cartridge is then inserted into the delivery unit which includes a state machine having an instruction set which is limited to precise instructions which are carried out as dictated by the programmed logic cartridge.

In the working embodiment particularly described herein, the system is capable of producing four fluid delivery profiles, coordinated in time, each having the following characteristics of amplitude and time resolution: The basic cycle can be up to twenty-four hours long, with a time resolution of one minute, and a flow rate range of 0 to 676 microliters per minute with a resolution of 1.5 microliters per minute, which amounts to a resolution of 1440 points in time and 451 points in amplitude; each basic cycle can be modified by an envelope scale modifier with a time resolution of one hour and a range of 31 days and the amplitude of the envelope modifier can be varied from 0 to 155% in multiples of 5%, which amounts to a resolution of 744 points in time and 31 points in amplitude (each resolvable amplitude/time element being called a segment); and the basic cycle and envelope scale modifier can be combined in any manner thereby resulting in unique profiles of up to 31 days in length.

Specific databases (indicated generally in FIGS. 1 and 2 as databases and assistive programs) are utilized at programming unit 13, and these are indicated in the functional flow chart of FIG. 8A as patient database 22a, drug database 22b, fluid path database 74, pump database 76, protocol database 24a, and archival database 78. The fluid path database provides information related to IV tube sizes used for a particular patient, while the pump database provides inventory control for pumps in use and the archival database provides a library of particular profiles used on particular patients.

Since the software within the general-purpose computer has complete "knowledge" of the elecronic circuitry which resides within the electronic hardware of the pump, any delivery profile which is designed, or established, on the general purpose computer can be completely "tested" or simulated by the general purpose computer before it is programmed into the logic cartridge and the logic cartridge utilized at the delivery unit, or pump.

In the specific embodiment described herein, the state machine is defined functionally (and completely) by 32 instructions which, when used in proper sequence, causes the pump to perform all of its required tasks.

Each of the 32 instructions is carried to the pump by an eight bit byte contained at one address location within the logic cartridge. The state machine is designed so that it recognizes these instructions, and can act upon them and their accompanying data bytes in a way that causes the motive output of the state machine to cause delivery of fluid just as was specified by the designer at the general purpose computer.

The electronic hardware at the state machine faithfully executes the special purpose instruction set of the pump and no other extraneous data to thus enhance safety. Thus, the state machine codes are a special purpose assembly language in the same sense that a particular computer is defined by its assembly language. FIG. 9 lists all data which travels from the computer to the pump coded into the logic (PROM) cartridge.

The firmware instruction set is thus used to control the actions of the state machine, and provides, for example, a means for setting delivery, quanta, envelopes, and multipliers, setting program counters, starting and stopping program counters, setting up a diagnostic QEM register, simulating stop and go buttons, and controlling the audible indicator, or beeper. Instructions are one byte (eight bits) long, and use odd parity in the high-order bit (bit 7 refers to the high-order bit, and bit 0 refers to the low-order bit).

As indicated in FIG. 9, which lists all data which is presented by the computer to the delivery unit by being coded into the logic cartridge, the instructions are broken into three groups. Group One has bits 5 and 6 set to 00, and is the "Move To Holding Register" (MTHR) instruction. Group Two has bit 6 set at 1, and is the "Deliver" (DEL) instruction. Group Three contains all other instructions, has bits 6 and 5 set at 01, and is the "Command" (CMD) instruction.

The following table lists all Group Three instructions, mnemonics, descriptions and actual values (after parity has been applied and including bits 5 and 6):

| COMMAND CODE | | |
|---|---|---|
| PROM DATA | NMEM | DESCRIPTION |
| 20 | INI | Set Initialization Program Counter |
| A1 | MIN | Set Minute Program Counter |
| A2 | DAY | Set Day Program Counter |
| 23 | DMD | Set Demand Program Counter |
| A4 | SINI | Start INI Counter/Set Pattern 0 IF INI |
| 25 | SMIN | Start MIN Counter |
| 26 | SDAY | Start Day Counter |
| A7 | SDMD | Start DMD Counter |
| A8 | HINI | Halt INI Counter |
| 29 | HMIN | Halt Min Counter |
| 2A | HDAY | Halt Day Counter |
| AB | HDMD | Halt DMD Counter |
| 2C | EB | Enable Beep |
| AD | DB | Disable Beep |
| AE | BIE | Beep If Enabled |
| 2F | PLU | Enable Plunger Detect Mode |
| B0 | SM0 | Set Multiplier For Channel 0 |
| 31 | SM1 | Set Multiplier For Channel 1/Diagnostic |
| 32 | SM2 | Set Multiplier For Channel 2 |
| B3 | SM3 | Set Multiplier For Channel 3/Spare Register |
| 34 | SE0 | Set Envelope For Channel 0 |
| B5 | SE1 | Set Envelope For Channel 1/Diagnostic |
| B6 | SE2 | Set Envelope For Channel 2 |
| 37 | SE3 | Set Envelope For Channel 3/Spare Register |
| 38 | TPE | Terminate Instruction Execution |
| B9 | CLRQ | Clear The QQ Register |
| BA | PRE | Set Motor Step Energy Level |
| 3B | — | Not Used |
| BC | GO | Same As Pressing "GO" Button |
| 3D | STP | Same As Pressing "STOP" Button |
| 3E | SND | No Operation |
| BF | NOP | No Operation |
| FF | HDE | Hard Error |

It is meant to be realized that the instruction set above set forth is for purpose of illustration of how a particular logic cartridge can be programmed for a particular use according to this invention, and accordingly, this invention is not meant to be limited to the particular instruction set as set forth.

The software which runs on the general purpose computer allows safe and effective dispensing of multiple therapeutic agents in busy environments. The functional flow diagram for effecting programming of a logic cartridge is shown in FIGS. 8A through 8D. As shown, three levels of passwords are utilized, thereby limiting access to qualified individuals; six relevant databases are maintained (thus, cross-checks for safety purposes as well as comprehensive administrative record keeping are accomplished at the same time a delivery profile is designed); human decisions (operator action) must be made whenever the computer software detects a questionable or potentially dangerous condition in the design of the profile; when profile design is complete, the computer validates the profile to ensure that arithmetic, procedural, or conceptual errors have not been made; the computer allows syringe changes (for the plurality of syringes) to be coordinated (and thus results in an efficient use of time); the computer program contains a simulator which allows the profile to be tested in software before it is passed to the pump by the logic cartridge (each segment for up to 31 days of run time can be calculated in faster computer time so that the software knows exactly what amount of fluid the pump will produce for each moment in time beforehand); the output from the simulator program is compared point by point with the designed profile as maintained in each of the delivery segments by the cross-check routine (the simulator combined with the cross-check amounts to both a check of predicted performance in the pump, as well as an overall check on the integrity of the software and the general purpose computer in which the software is running); the computer produces a hard-copy printed summary of the simulator run (this tells the human operator exactly what the pump hardware will produce hour-by-hour for the whole profile's duration and places the burden for acceptance of the computer's work on the operator's shoulders); the logic cartridge is finally programmed, or "burned", and then read back and compared with its own generating file to assure integrity; and by providing a drug administration report a simple and graphic method is provided by which the pump then seen can be quickly compared with a piece of paper to immediately make it apparent that infusion is proceeding either properly or improperly.

For purposes of further illustration, assume the following:

| Channel | Infusate | Drug | Units | Volume (ML) | Cycle Lengths | |
|---------|----------|------|-------|-------------|----------------|---|
| A | DRUG A | 10 | mg | 30 | Basic Cycle | 24 hrs |
| B | DRUG B | 20 | mg | 30 | Demand Cycle | 0 min |
| C | DRUG C | 10 | mg | 20 | Loading Cycle | 60 min |
| D | DRUG D | 30 | ml | 30 | Profile Duration | 5 days 0 hours | and that the following is meant to occur:

| Ch. | Start Time hr/mn | End Time hr/mn | Duration | Dose mg | Actual Dose mg | Shape | Start Flow ml/hr | End Flow ml/hr |
|-----|------|------|------|------|------|------|------|------|
| A | 0:00 | 24:00 | 24:00 | 100.00 | 100.00 | linear | 12.50 | 12.50 |
| B | 0:00 | 1:54 | 1:54 | 30.00 | 29.99 | linear | 23.68 | 23.68 |
| B | 3:00 | 4:54 | 1:54 | 30.00 | 29.99 | linear | 23.68 | 23.68 |
| B | 6:00 | 7:54 | 1:54 | 30.00 | 29.99 | linear | 23.68 | 23.68 |
| B | 9:00 | 10:54 | 1:54 | 30.00 | 29.99 | linear | 23.68 | 23.68 |
| B | 12:00 | 13:54 | 1:54 | 30.00 | 29.99 | linear | 23.68 | 23.68 |
| B | 15:00 | 16:54 | 1:54 | 30.00 | 29.99 | linear | 23.68 | 23.68 |
| B | 18:00 | 19:54 | 1:54 | 30.00 | 29.99 | linear | 23.68 | 23.68 |
| B | 21:00 | 22:54 | 1:54 | 30.00 | 29.99 | linear | 23.68 | 23.68 |
| C | 2:00 | 2:54 | 0:54 | 2.50 | 2.50 | linear | 5.56 | 5.56 |
| C | 5:00 | 5:54 | 0:54 | 2.50 | 2.50 | linear | 5.56 | 5.56 |
| C | 8:00 | 8:54 | 0:54 | 2.50 | 2.50 | linear | 5.56 | 5.56 |
| C | 11:00 | 11:54 | 0:54 | 2.50 | 2.50 | linear | 5.56 | 5.56 |
| C | 14:00 | 14:54 | 0:54 | 2.50 | 2.50 | linear | 5.56 | 5.56 |
| C | 17:00 | 17:54 | 0:54 | 2.50 | 2.50 | linear | 5.56 | 5.56 |
| C | 20:00 | 20:54 | 0:54 | 2.50 | 2.50 | linear | 5.56 | 5.56 |
| C | 23:00 | 23:54 | 0:54 | 2.50 | 2.50 | linear | 5.56 | 5.56 |
| D | 1:56 | 2:00 | 0:04 | 1.67 | 1.66 | linear | 25.00 | 25.00 |
| D | 2:56 | 3:00 | 0:04 | 1.67 | 1.66 | linear | 25.00 | 25.00 |
| D | 4:56 | 5:00 | 0:04 | 1.67 | 1.66 | linear | 25.00 | 25.00 |
| D | 5:56 | 6:00 | 0:04 | 1.67 | 1.66 | linear | 25.00 | 25.00 |
| D | 7:56 | 8:00 | 0:04 | 1.67 | 1.66 | linear | 25.00 | 25.00 |
| D | 8:56 | 9:00 | 0:04 | 1.67 | 1.66 | linear | 25.00 | 25.00 |
| D | 10:56 | 11:00 | 0:04 | 1.67 | 1.66 | linear | 25.00 | 25.00 |
| D | 11:56 | 12:00 | 0:04 | 1.67 | 1.66 | linear | 25.00 | 25.00 |
| D | 13:56 | 14:00 | 0:04 | 1.67 | 1.66 | linear | 25.00 | 25.00 |
| D | 14:56 | 15:00 | 0:04 | 1.67 | 1.66 | linear | 25.00 | 25.00 |
| D | 16:56 | 17:00 | 0:04 | 1.67 | 1.66 | linear | 25.00 | 25.00 |
| D | 17:56 | 18:00 | 0:04 | 1.67 | 1.66 | linear | 25.00 | 25.00 |
| D | 19:56 | 20:00 | 0:04 | 1.67 | 1.66 | linear | 25.00 | 25.00 |
| D | 20:56 | 21:00 | 0:04 | 1.67 | 1.66 | linear | 25.00 | 25.00 |
| D | 22:56 | 23:00 | 0:04 | 1.67 | 1.66 | linear | 25.00 | 25.00 |
| D | 23:56 | 24:00 | 0:04 | 1.67 | 1.66 | linear | 25.00 | 25.00 |

A basic cycle delivery graph based upon the foregoing is illustrated in FIG. 10, and a basic cycle timing graph is set forth in FIG. 11.

Based upon the foregoing, a quick screen report and simulator report would appear substantially as follows:

Quick Screen Report

Patient ID: 1002  Name: RICH  Location: IMI-2
Profile: 3  Dr.: WHO  Pharmacist: ME
Profile Duration: 5-0 days-hrs.  Start Delay: 1 hrs.
Profile: Repeats  When Stop is Pressed, Clock: Stops
Pump Serial Number: 4567

| Infusate-A DRUG A | Infusate-B DRUG B | Infusate-C DRUG C | Infusate-D DRUG D |
|---|---|---|---|
| Syringe Amts 30 ml 10 mg | Syringe Amts 30 ml 20 mg | Syringe Amts 20 ml 10 mg | Syringe Amts 30 ml 30 ml |
| Loading Dose 2 mg :10 | Loading Dose 2 mg :30 | Loading Dose 5 mg :30 | Loading Dose 0 ml :0 |
| Act. Loading Dose 2 mg | Act. Loading Dose 2.01 mg | Act. Loading Dose 5 mg | Act. Loading Dose 0 ml |
| Infusion Model Continuous Delivery | Infusion Model Alternating Delivery | Infusion Model Alternating Delivery | Infusion Model Flush Delivery |
| Dose 5 mg/day | Dose 12 mg/day | Dose 1 mg/day | Dose 0.5 ml/flush |

-continued

Quick Screen Report

Patient ID: 1002  Name: RICH  Location: IMI-2
Profile: 3  Dr.: WHO  Pharmacist: ME
Profile Duration: 5-0 days-hrs.  Start Delay: 1 hrs.
Profile: Repeats  When Stop is Pressed, Clock: Stops
Pump Serial Number: 4567

| Infusate-A DRUG A | Infusate-B DRUG B | Infusate-C DRUG C | Infusate-D DRUG D |
|---|---|---|---|
| Act. Delivery Dose 5 mg | Act. Delivery Dose 12 mg | Act. Delivery Dose 1 mg | Act. Delivery Dose 0.5 ml Pause: :2 |
|  | Duration: 2: 0 Flush: Yes | Duration: 1: 0 Flush: Yes | Duration: :4 |
| Pressure: HI Turn-ON: 1-0 d-h Turn-OFF: 6-9 d-h | Pressure: HI Turn-ON: 1-0 d-h Turn-OFF: 6-0 d-h | Pressure: HI Turn-ON: 1-0 d-h Turn-OFF: 6-0 d-h | Pressure: HI Turn-ON: AUTO d-h Turn-OFF: AUTO d-h |
| Sry. Chg: 1-12 d-h | Sry. Chg: 1-12 d-h | Sry. Chg: 1-12 d-h | Sry. Chg: 1-12 d-h |

SIMULATOR REPORT

| Chan | Infusate | Concentration | Press | Loading Dose | dmd | env |
|------|----------|---------------|-------|--------------|-----|-----|
| A: | DRUG A | 0.33 mg/ml | HI | 2.00 mg | NO | YES |

-continued

SIMULATOR REPORT

| Chan | Infusate | Concentration | Press | Loading Dose | dmd | env |
|---|---|---|---|---|---|---|
| B: | DRUG B | 0.67 mg/ml | HI | 2.01 mg | NO | YES |
| C: | DRUG C | 0.50 mg/ml | HI | 5.00 mg | NO | YES |
| D: | DRUG D | 1.00 ml/ml | HI | 0.00 | NO | YES |

Profile length is 5 days and 0 hours. Start of profile delayed 1 hr. Profile Repeats. Clock stops when STOP is pressed.

ACTUAL DELIVERY

| Day | Hr to Hr | CHANNEL A Dose (mg) | CHANNEL B Dose (mg) | CHANNEL C Dose (mg) | CHANNEL D Dose (ml) |
|---|---|---|---|---|---|
| 1 | 0 to 8 | 3.63 | 6.12 | 5.25 | 2.48 |
|   | 8 to 16 | 1.67 | 3.79 | 0.38 | 2.49 |
|   | 16 to 24 | 1.67 | 3.71 | 0.37 | 2.98 |
| 1 | TOTAL | 6.96 | 13.61 | 6.00 | 7.95 |
| 2 | 0 to 8 | 1.67 | 4.50 | 0.25 | 2.48 |
|   | 8 to 16 | 1.67 | 3.79 | 0.38 | 2.49 |
|   | 16 to 24 | 1.67 | 3.71 | 0.37 | 2.98 |
| 2 | TOTAL | 5.00 | 12.00 | 1.00 | 7.95 |
| 3 | 0 to 8 | 1.67 | 4.50 | 0.25 | 2.48 |
|   | 8 to 16 | 1.67 | 3.79 | 0.38 | 2.49 |
|   | 16 to 24 | 1.67 | 3.71 | 0.37 | 2.98 |
| 3 | TOTAL | 5.00 | 12.00 | 1.00 | 7.95 |
| 4 | 0 to 8 | 1.67 | 4.50 | 0.25 | 2.48 |
|   | 8 to 16 | 1.67 | 3.79 | 0.38 | 2.49 |
|   | 16 to 24 | 1.67 | 3.71 | 0.37 | 2.98 |
| 4 | TOTAL | 5.00 | 12.00 | 1.00 | 7.95 |
| 5 | 0 to 8 | 1.67 | 4.50 | 0.25 | 2.48 |
|   | 8 to 16 | 1.67 | 3.79 | 0.38 | 2.49 |
|   | 16 to 24 | 1.67 | 3.71 | 0.37 | 2.98 |
| 5 | TOTAL | 5.00 | 12.00 | 1.00 | 7.95 |
|   | PROFILE TOTAL | 26.96 | 61.60 | 10.00 | 39.76 |

Also based upon the foregoing, a user would be able to visually ascertain the amount of therapeutic agent in each channel by viewing the top of the delivery unit when openings are provided for syringe viewing, as indicated in FIGS. 12A through 12E, and proper operation can be ascertained by comparing the viewed actual results with the printed drug administration report. As indicated, each FIGURE illustrates a different specific time during a five day infusion period.

Of major importance is the fact that this capability has been designed without requiring microprocessors in the controller. While microprocessors are powerful, they can have a significant limitation of lacking software provability (at least without use of multiple units to provide a cross-check), as well as being incapable of providing a device with sufficient safety and long-time reliability required for long, high resolution, computer delivery requirements (known as profiles).

All of the "intelligent" features are included in the programming unit. This allows the delivery unit (which is the key component in the patient's view) to be kept simple, have a low cost, and yet be highly reliable.

The programming unit is far more powerful and friendly than known systems, which attempt to fit sophisticated controls into small and thus compromise both size and user friendliness. In addition, the system of this invention, uses partitioning (i.e., programming in a separate unit from that of the delivery unit) which is a major departure from known practice.

The programming unit prompts the user (such as a pharmacist) for patient and prescription data. Basic protocol information may be requested from a database to speed data entry. The protocol outline asks only for the minimum amount of data needed to individualize dosages to the patient.

Protocols are derived from published sources, third parties, or are developed by the user. In the latter case, friendly software is preferably provided to assist the user by asking a series of questions. All protocol entries and change may be preferably date/time coded to provide a complete audit trail.

If requested, the computer queries a drug database to check for dosage range errors and for compliance with package insert labeling. It also checks for possible adverse drug interactions. The user may over-ride certain types of warnings by providing signature for the audit trail held in the permanent patient record.

The provided software may, if desired, cause the computer to look up the patient's history on the patient database to check for consistency. Again, the user may over-ride certain warnings with appropriate security precautions. The patient's records are automatically updated upon the user verification of correct entry.

The computer can be used not only to manage each of the infused drugs, but other drugs as well. It also charts the responses of the patient to therapy, or any laboratory measurements.

The computer is thus utilized as far more than just a delivery unit programmer. It is a comprehensive medication management system. The user can also ask the computer to use pharmacokinetic algorithms to help derive optimum profiles for a patient. The algorithm prompts for laboratory data and may, if requested, remind the user of the correct sampling protocol.

The computer writes coded data into the logic cartridge only after the data has been verified and the delivery unit operation simulated and cross-checked against the original desired discrete flow segments using the program established by the computer to thereby insure safety of operation. The computer also then causes a label to be printed, in appropriate pharmacy form, for placement on the cartridge. Finally, the computer may cause a hard copy of the patient's updated record to be printed, and copies all data into the patient database.

The programmable logic cartridge is a non-volatile memory (it does not lose contents with power loss). It may be used either as a one-time disposable, or as a reprogrammable cartridge. The former provides relatively low cost with ultimate data security. Disposablity assures the least chance of a mixup, which is possible with reuse. The old cartridges may be included in the patient's permanent physical file for medico-legal backup.

Although microprocessor-based devices use read-only memories, they are used for the code of the processor (the user's program), but not for the user's delivery data—which is in the radom-access memory (RAM) unit with presently known systems. In addition, known systems, despite containing one or two microprocessors, have only a very limited "vocabulary" of permissible flow profiles. To change the profile, the machine code must be rewritten, which is quite difficult and error-prone, and cannot normally be done by the user. Such systems are therefore rigidly limited in capability despite the use of relatively complex computing chips which are required to manage these very simple functions, with most of the sophistication of such a process being used to manage manual controls and displays.

Unlike the more commonly used RAM unit which is designed for high-speed writing as well as reading at low voltages and is thus relatively susceptible to electrical noise as well as being volatile, the logic cartridge used in this invention is exceedingly resistant to environmental electromagnetic noise.

Most significantly, the logic memory unit is used as a configurable logic, and not as simple table of parameters to be looked up. This gives the system of this invention enhanced programming power with the capability of providing multichannel, complex, high resolution, long profiles in a lightweight (and thus wearable, if desired) delivery unit.

As can be appreciated from the foregoing, this invention provides an improved and safety enhance system and method for application of a therapeutic agent to a patient.

What is claimed is:

1. A device for effecting application of a therapeutic agent to a patient, said device comprising:
    application means including delivery means adapted to deliver a preselected therapeutic agent to a patient with said delivery means having flow control means for controlling the flow of said therapeutic agent from said delivery means, and said application means also including electronic control means for controlling said flow control means with said electronic control means including removable programmable means for establishing a flow profile for said delivery means when said programmable means is programmed and operatively positioned at said application means; and
    programming means operationally independent of said application means for establishing a then selected flow profile program and programming said program into said programmable means while said programmable means is removed from said application means, said programming means also simulating operation of said delivery means according to said then selected flow profile program.

2. The device of claim 1 wherein said programmable means is an operationally non-volatile cartridge movable between said application means and said programming means, and wherein said programming means is a general-purpose computer.

3. The device of claim 2 wherein said computer includes database means to provide information so that said computer is responsive to at least patient information, drug information, and delivery unit operating instructions when establishing and simulating said program.

4. The device of claim 1 wherein said programming means includes means to store a series of instructions available to said electronic control means for operation of said flow control means, and wherein said progamming means utilizes said series of instructions along with said program for simulation purposes.

5. The decive of claim 1 wherein said programming means simulates operation of said delivery means prior to programming said program into said programmable means.

6. The device of claim 5 wherein said programming means also calculates proposed delivery of therapeutic agent according to said then selected profile, calculates delivery according to said simulated operation of said delivery means, and compares the calculated results to provide a cross-check function for enhancing safety of operation of said application means.

7. The device of claim 1 wherein said program established by said programming means is coded information when programmed into said programmable means, and wherein said coded information into said progammable means includes patient ID information to further enhance seccuity and safety of subsequent delivery of therapeutic agent by said application means.

8. The device of claim 1 wherein said application means includes refillable reservoir means for containing said therapeutic agent to be delivered by said delivery means, and wherein said device also includes means for preparation of a refill schedule for said reservoir means.

9. The device of claim 1 wherein said programming means also causes printing of at least one of a report of said simulation, a report of therapeutic agent administration, and therapeutic agent administration, and therapeutic agent information carrying labels.

10. The device of claim 1 wherein said delivery means includes channel means defining a plurality of channel for seprately delivering therapeutic agent, wherein said flow control means includes a plurality of controllable units each of which is associated with a different one of said channels, wherein said programmable means controls each of said controllable units, wherein said programming means programs said programmable means so that each of said units operates independently of one another whereby independent flow profile are established for each of said channels, and wherein said programming means simulates operation of each of said controllable units to thereby substantially assure safety of delivery from all of said channels.

11. The device of claim 10 wherein said programming means also provides calculated results of flow profile with respect to each of said channels and calculated results of simulated operation with respect to each of said channels, and providing a cross-check between said calculated results to thereby further assure safety of delivery from all of said channels.

12. A device for effecting application of a therapeutic agent to a patient, said device comprising:
    drive means for controlling delivery of a preselected therapeutic agent to a patient;

electronic means including a removable programmable logic cartridge that is substantially operationally non-volatile for being programmed with a flow profile to control operation of said flow drive means when said programmable logic cartridge is programmed and operatively positioned; and computer means for establishing a program of a then selected flow profile and receiving said removable programmable logic cartridge and programming the same with a then selected flow profile based upon predetermined parameters of patient need and therapeutic agent capabilities, said computer means also simulating operation of said drive means according to said program prior to programming of said programmable logic cartridge by said computer means to establish simulated operation results and cross-checking said simulated operation results with said then selected flow profile to thereby enhance safety of delivery of therapeutic agent to a patient.

13. The device of claim 12 wherein said computer means includes database means connected with said computer to provide information thereto so that said computer is responsive to at least patient information, durg information, and delivery unit operation instructions when establishing and simulating said program, and wherein said computer means causes printing of at least one of reports and labels for use in association with delivery of therapeutic agent from said device.

14. The device of claim 12 wherein said device has a plurality of channels for separately delivering therapeutic agent to a patient, wherein said drive means includes a separate driver associated with each of said channels with operation of each of said drivers being controlled by said programmable logic cartridge, wherein said programmable logic cartridge is programmed by said computer means to effect a separate flow profile for each of said channels, and wherein said computer means simulates operation of each of said controllable units to establish simulated operation results and provides cross-checking of said simulated operation results with said then selected flow profile with respect to each of said channels to thereby enhance safety of delivery from all of said channels.

15. In a system for effecting application of a therapeutic agent with known therapeutic properties to a patient utilizing therapeutic agent application means, wherein the improvement comprises:

control means for controlling operation of said application means, and a programming system for programming said control means, said programming system including program establishing means for establishing a desired program and means for cross-checking said desired program with said therapeutic properties and said patient history to thereby enhance saftey of delivery of the therapeutic agent to the patient.

16. The programming system of claim 15 wherein said desired program establishing means includes a computer for establishing said desired program therein, and for simulating operation of said control means according to said desired program.

17. The programming system of claim 16 wherein said computer also calculates the resullts of operation according to said desired program and according to said simulating operation and compares said calculated results to one another to further assure safe operation of said application means.

18. A method for effecting application of a therapeutic agent to a patient, said method comprising:

establishing parameters for safe application of said therapeutic agent to a patient;

providing delivery means adapted to deliver said therapeutic agent to a patient;

controlling operation of said delivery means through electronic control means that includes a removable programming element which, when operatively positioned, controls the flow of said therapeutic agent from said delivery means;

establishing a flow profile program through computer means and simulating operation of said delivery means through said computer means utilizing said flow profile program; and programmming said programmable element with said flow profile program through said computer means only if said simulation of operation of said delivery means through said computer means indicates that delivery of said therapeutic agent according to said flow profile program can be effected within said parameters.

19. The method of claim 18 wherein said method also includes calculating the results of fluid delivery using said established flow profile, calculating the results of fluid delivery adccording to said simulated operation of said delivery means, comparing the calculated results to determine difference therebetween, and utilizing any such differences greater than predetermined difference to further prevent programming of the programmable element.

20. The methods of claim 19 wherein said programmable element is an operatively non-volatile logic cartridge, and wherein said method includes programming said programmable logic cartrige while removed from said delivery means by use of a general-purpose computer.

21. The method of claim 20 wherein said method includes providing a delivery means having a plurality of channels through which therapeutic agent are separately conveyed for delivery to a patient, establishing a program for separately controlling the flow of therapeutic agent through each of channels by said programmable element, simulating operation through each of said channels according to said established program, and programming said programmable element to establish said separate flow profile for each of said channels only if simulation of said operation through all of said channels indicates that said flow through all of said channels can be safely effected.

22. The method of claim 21 wherein said method includes calculating the results of fluid delivery using said selected flow profile for each of plurality of channels, calculating the results of fluid delivery arising from said simulating operation, comparing the calculated results to determine therefrom differences indicative of unsafe flow through any said plurality of channels, and preventing programming of said programmable element if any said unsafe flow indication is determined.

23. A method for effecting application of a therapeutic agent to a patient, said method comprising:

selecting a desired flow profile for a preselected therapeutic agent with respect to a predetermined patient;

simulating a preselected operation of delivery of said therapeutic agent to a patient utilizing said selected profile;

calculating the results of fluid delivery using said selected flow profile and fluid delivery due to said simulated operation and comparing the same to determined differences therebetween;

determining from said simulation operation and said determined comparison differences whether said selected flow profile can be utilized to safely deliver therapeutic agent to a patient using said selected profile;

programming a logic cartridge that is operationally non-volatile to thereby provide said flow profile only if it has been determined that said selected profile can be safely utilized; and using said programmed logic cartridge to control flow of said predetermined therapeutic agent to said patient.

24. A method for effecting application of a therapeutic agent to a patient, said method comprising:

establishing parameters for the safe application of said agent to said patient;

simulating a preselected operation of delivery of said therapeutic agent to a patient utilizing said selected profile;

calculating the results of fluid delivery using said selected flow profile and fluid delivery due to said simulated operation and comparing the same to determined differences therebetween;

determining from said simulation operation and said determined comparison differences whether said selected flow profile can be utilized within said parameters to deliver therapeutic agent to a patient using said selected profile;

programming a logic cartridge that is operationally non-volatile to thereby provide said flow profile only if it has been determined that said selected profile can be safely utilized; and using said programmed logic cartridge to control flow of said predetermined therapeutic agent to said patient.

25. The method of claim 23 wherein said method includes printing an expected drug administration report and therapeutic agent information labels after programming of said logic cartridge to facilitate said use of said programmed logic cartridge.

* * * * *

UNITED STATES PATENT AND TRADEMARK OFFICE
CERTIFICATE OF CORRECTION

PATENT NO. : 5,088,981

DATED : February 18, 1992

INVENTOR(S) : Howson, et al.

It is certified that error appears in the above-indentified patent and that said Letters Patent is hereby corrected as shown below:

Column 1, line 11, insert a comma after the word "AGENT" and delete "Ser".

Column 1, line 12, delete the word "application" and replace it with the word "patent".

Column 1, line 20, delete the word "a" and replace it with the word "and".

Column 2, line 19, delete the word "system" and replace it with the word "systems".

Column 4, line 41, delete the word "difficultly" and replace it with the word "difficulty".

Column 4, line 41, delete the word (second in the line) "the" and replace it with the word "of".

Column 4, line 48, delete the word "reducting" and replace it with the word "reduction".

Column 4, line 48, insert a comma after the word "means".

Column 5, line 53, delete the word "a" and replace it with the word "an".

Column 10, line 57, delete the word "elecronic" and replace it with the word "electronic".

Column 15, line 60, insert after the word "small" the word "size".

UNITED STATES PATENT AND TRADEMARK OFFICE
CERTIFICATE OF CORRECTION

PATENT NO. : 5,088,981

DATED : February 18, 1992

INVENTOR(S) : Howson, et al.

It is certified that error appears in the above—identified patent and that said Letters Patent is hereby corrected as shown below:

Column 16, line 7, delete the word "change" and replace it with the word "changes".

Column 16, line 46, delete the word "user" and replace it with the word "users".

Column 17, line 33, insert after the word "as" the word "a".

Column 17, line 40, delete the word "enhance" and replace it with the word "enhanced".

Column 17, line 67, insert after the word "non-volatile" the word "logic".

Column 18, line 15, delete the word "decive" and replace it with the word "device".

Column 18, line 41, delete after "agent" the word "administration" and replace it with the word "information".

Column 18, line 45, delete the word "channel" and replace it with the word "channels".

Column 18, line 45, delete the word "seprately" and replace it with the word separately".

Column 18, line 45, delete the word "agent" and replace it with the word "agents".

Column 18, line 53, delete the word "profile" and replace it with the word "profiles".

UNITED STATES PATENT AND TRADEMARK OFFICE
CERTIFICATE OF CORRECTION

PATENT NO. : 5,088,981
DATED : February 18, 1992
INVENTOR(S) : Howson, et al.

It is certified that error appears in the above—identified patent and that said Letters Patent is hereby corrected as shown below:

Column 19, line 56, delete the word "saftey" and replace it
    with the word "safety".

Column 19, line 64, delete the word "resullts" and replace it
    with the word "results".

Column 20, line 9, delete the word "programming" and replace
    it with the word "programmable".

Column 20, line 28, delete the word "difference" and replace
    it with the word "differences".

Column 20, line 29, delete the word "difference" and replace
    it with the word "differences".

Column 20, line 40, delete the word "agent" and replace it
    with the word "agents".

Signed and Sealed this

Seventh Day of December, 1993

Attest:

BRUCE LEHMAN

*Attesting Officer*   *Commissioner of Patents and Trademarks*